(12) United States Patent
Borgesen

(10) Patent No.: US 6,905,474 B2
(45) Date of Patent: *Jun. 14, 2005

(54) FLUID SHUNT SYSTEM AND A METHOD FOR THE TREATMENT OF HYDROCEPHALUS

(75) Inventor: Svend Erik Borgesen, Kokkedal (DK)

(73) Assignee: CSF Dynamic A/S, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/949,993

(22) Filed: Sep. 12, 2001

(65) Prior Publication Data

US 2002/0045847 A1 Apr. 18, 2002

Related U.S. Application Data

(60) Provisional application No. 60/231,578, filed on Sep. 11, 2000.

(51) Int. Cl.⁷ .......................... A61M 5/00; A61M 37/00
(52) U.S. Cl. ............................. 604/9; 604/8; 604/6.16
(58) Field of Search ........................... 604/8–10, 6.16, 604/264, 185, 247; 137/843

(56) References Cited

U.S. PATENT DOCUMENTS

| 2,969,066 A | 1/1961 | Holter et al. |
| 3,233,610 A | 2/1966 | Wade |

(Continued)

FOREIGN PATENT DOCUMENTS

| DE | 198 20 808 | 11/1999 |
| EP | 0 066 685 | 12/1982 |
| EP | 0 086 685 B1 | 12/1982 |
| EP | 0 344 895 | 12/1989 |
| EP | 0 363 873 | 4/1990 |
| EP | 0 409 511 | 1/1991 |
| EP | 0 982 048 A1 | 3/2000 |
| GB | 2 330 078 | 4/1999 |
| SU | 1176894 A | 9/1985 |
| WO | 96/37144 | 11/1996 |
| WO | WO 98/02202 A1 | 1/1998 |
| WO | 98/11934 | 3/1998 |

(Continued)

OTHER PUBLICATIONS

Becker, et al, "Investigation of Sagittal Sinus For Venous Shunt in Hydrocephalus". Surg. Forum. (1965). 16:440–442.

(Continued)

*Primary Examiner*—Angela D. Sykes
*Assistant Examiner*—Leslie R. Deak
(74) *Attorney, Agent, or Firm*—Browdy and Neimark, P.L.L.C.

(57) ABSTRACT

A cerebrospinal fluid shunt system comprises a brain ventricle catheter (15) to insert into the brain ventricle (21) so as to drain cerebrospinal fluid from the brain ventricle, a sinus catheter (18) to insert into the sinus sagittalis system (22) for feeding the cerebrospinal fluid into the sinus sagittalis system, a shunt body member (10) connected at one end thereof to said brain ventricle catheter and at another end thereof to said sinus catheter system to provide fluidic communication between said brain ventricle catheter (15) and said sinus catheter (18), and a flow restriction (16) defined within the shunt body member (10) to maintain a resistance to fluid flow of the shunt system of less than 8 mm Hg/ml/min, such as 2–7 or 4–6 and preferably about 5 mm Hg/ml/min. When the shunt system is implanted the shunt body member (10) is placed subcutaneously on top of the calvarium of a patient, behind the coronal suture on one of side of the sagittal suture. One end of each of the catheters (15, 18) is then connected to a respective end of the shunt body member (10), and a second end of each catheter is inserted in the right ventricle (21) and in the sinus sagittalis system (22), respectively, via holes bored in the scull (19).

39 Claims, 4 Drawing Sheets

U.S. PATENT DOCUMENTS

| | | | |
|---|---|---|---|
| 3,566,875 A | | 3/1971 | Stoehr |
| 3,583,387 A | * | 6/1971 | Garner et al. ............... 600/561 |
| 3,894,541 A | | 7/1975 | El-Shafei |
| 4,182,343 A | | 1/1980 | Inaba |
| 4,377,169 A | | 3/1983 | Banks |
| 4,382,445 A | * | 5/1983 | Sommers ....................... 604/8 |
| 4,438,773 A | | 3/1984 | Letterio |
| 4,500,311 A | | 2/1985 | Redmond et al. |
| 4,578,057 A | | 3/1986 | Sussman |
| 4,605,395 A | | 8/1986 | Rose et al. |
| 4,646,752 A | | 3/1987 | Swann et al. |
| 4,781,673 A | | 11/1988 | Watanabe |
| 4,781,674 A | | 11/1988 | Redmond et al. |
| 4,784,648 A | | 11/1988 | Singh et al. |
| 4,903,707 A | | 2/1990 | Knute et al. |
| 4,904,236 A | | 2/1990 | Redmond et al. |
| 5,000,731 A | | 3/1991 | Wong et al. |
| 5,042,974 A | | 8/1991 | Agarwal |
| 5,054,497 A | | 10/1991 | Kapp et al. |
| 5,891,100 A | | 4/1999 | Fleckenstein |
| 5,980,480 A | | 11/1999 | Rubenstein et al. |
| 6,264,625 B1 | | 7/2001 | Rubenstein et al. |
| 6,283,934 B1 | | 9/2001 | Børgesen |
| 6,383,159 B1 | | 5/2002 | Saul et al. |
| 6,689,085 B1 | | 2/2004 | Rubenstein et al. |

FOREIGN PATENT DOCUMENTS

| | | |
|---|---|---|
| WO | 99/24097 | 5/1999 |
| WO | 99/30746 | 6/1999 |
| WO | 99/58053 | 11/1999 |
| WO | WO 01/54752 A1 | 8/2001 |
| WO | WO 01/54768 A1 | 8/2001 |
| WO | WO 02/36193 A1 | 5/2002 |
| WO | WO 03/015710 A2 | 2/2003 |

OTHER PUBLICATIONS

Bersnev, et al, "Treatment Of Hydrocephalus By Ventricle–Sinus Trans–Anastomosis". Zhumal Vaprosy Neiokhirurgii Imeni N.N. Burdenko. (Jul.–Aug. 1989), 4:17–19.

Borgesen, et al, "Shunting To The Sagittal Sinus". Intracranial Pressure and Brain Biochemical Monitoring. (2002) 84:11–14.

El Shafei, "Ventriculo–Venous Shunt to the Proximal Segment of an Occluded Neck Vein". Surg. Neurol. (May 1975). 3: 237–244.

El Shafei, "Ventriculovenous Shunt to the Proximal Segment of a Legated Neck Vein". Childs Brain. (1975) 1:311–323.

El Shafei, eta L, "Ventriculojugular Shunt Against the Direction of Blood Flow. I. Role of the internal jugular vein as an antisiphonage device". Child's Nerv. Syst. (1987). 3(5):282–284.

El Shafei, et al "Ventriculojugular Shut Against the Direction of Blood Flow. II. Theroretical ans experimental basis for shunting the cerebrospinal fluid against the direction of blood flow". Child's Nerv. Syst. (1987). 3(5):285–291.

El Shafei, "Ventriculojugular Shunt Against the Direction of Blood Flow. III. Operative technique and results". Child's Nerv. Syst. (1987), 3(5):342–349.

El Shafei, "Ventriculovenous Shunt Against The Direction Of Blood Flow: A New Approach For Shunting The Cerebrospinal Fluid To The Venous Circulation". Child's Nerv. Syst. (1985), 1:200–207.

El Shafei, et al "Ventriculojugular Shunt Against the Direction of Blood Flow. IV. Technical Modifications and policy for treatment". Child's Nerv. Syst. 91991). 7:197–204.

El Shafei et al "The retrograde ventriculosinus shunt: concept and technique for treatment of hydrocephalus by shunting the cerebrospinal fluid to the superior sagittal sinus against the dirction of blod flw:Preliminary Report". Child's Nerv. Syst. (2001) 17:457–465.

Frim, et al, "Measurements of Intraventricular Pressure in a Patient shunted From The Ventricle To The Internal Jugular Vein Against The Direction Of Blood Flow (the El–Shafei Shunt)". Child's Nerv. Syst. (2001). 17:379–381.

Lee, et al "Ventriculoatrial Shunt via the Transverse Sinus: Technical Note". Neurosurgery (1992). 30(2):249–252.

Mathews, et al, "Ventriculo–Sagittal Sinus Shunting In Adult Hydrocephalus". International Congress of Neurologicall Surgery, $5^{th}$ Tokyo (1973), p. 135. Abstract.

Sharkey, "Ventriculosagittal–Sinus Shunt". J. Neurosurgery. (Apr. 1965). 22:362–367.

A. Aschoff et al., "Overdrainage and Shunt technolgy," *Child's Nerv. Syst.* (1995) 11:193–202.

S.E. Børgesen et al., "Measurement of Resistance to CSF Outflow—Clinical Experience in 333 Patients," *Intracranial Pressure VII*, pp. 353–355, 1989.

S.E. Børgesen et al., "Relationships Between Intracranial Pressure, Ventricular Size and Resistance to CSF Outflow," *J. Neurosurg.*, 67:535–539, 1987.

S.E. Børgesen et al., "Measurement of Resistance to CSF Outflow by Subarachnoid Perfusion," Outflow of Cerebrospinal Fluid, *Alfred Benzon Symposium 27*, pp. 121–133, 1989.

S.E. Børgesen et al., "The Predictive Value of Conductance to Outflow of CSF in Normal Pressure Hydrocephalus," *Brain* 105, pp. 65–86, 1982.

J. M. Drake et al., *The Shunt Book*, p. 146, 1985.

C.J. Hash et al., "Ventricle to Sagittal Sinus for Hydrocephalus, " *Neurosurgery*, vol. 4:5, pp. 394–400, 1979.

H.L. Wen, "Ventriculo–Superior Sagittal Sinus Shunt for Hydrocephalus," *Surgical Neurology*, vol. 17:6, pp. 432–434, Jun. 1982.

A. Aschoff et al., "The history of valved shunts. A review on 177 historical, recently available and prototype valves," *XXV Annual Congress of Int'l Society of Pediatric Neurosurgeons*, 6 pp., Verona 13–$18^{th}$ Sep. 1997.

Michael J. Albeck et al., "Age dependency of resistance to cerebrospinal fluid outflow", J. Neurosurg. 89:275–278 (1998).

* cited by examiner

FLUID SHUNT SYSTEM AND A METHOD FOR THE TREATMENT OF HYDROCEPHALUS

This application claims the benefit of U.S. Provisional Application No. 60/231,578, filed Sep. 11, 2000 now abandoned.

FIELD OF THE INVENTION

The present invention relates to a cerebrospinal fluid shunt system for shunting cerebrospinal fluid from the brain ventricles to sinus sagittalis (including sinus transversus) in patients with so-called normal pressure hydrocephalus and in children with a combination of widely dilated ventricles and low intracranial pressure.

BACKGROUND OF THE INVENTION

Cerebrospinal fluid is formed in the ventricular system irrespective of the intracranial pressure (ICP). The formation rate is constant, with a range of 0.3–0.4 ml/min. (Børgesen and Gjerris 1987). Hydrocephalus, i.e. a pathological increase in the amount of intracranially located cerebrospinal fluid, arise when the outflow of the cerebrospinal fluid is obstructed, leading to an increase in the intracranial pressure and in the amount of intracranially located cerebrospinal fluid. The obstruction may be localized in the aqueduct or the IV ventricle or in the normal resorption sites in villi arachnoidales in connection with the sagittal sinus. Pathoanatomically, hydrocephalus is divided in communicating or non-communicating hydrocephalus dependent whether there is passage between the ventricular system and sinus sagittalis or not. Communicating hydrocephalus, which is generally caused by obstruction located in the villi arachnoidales for example due to fibrosis formed in response to bleeding in the liquor, is the most common form of hydrocephalus.

The treatment of hydrocephalus aims at reducing the intracranial pressure to normal, physiological values and thereby also reducing the amount of cerebrospinal fluid towards normal, physiological values. This is obtained by deducting cerebrospinal fluid (CSF) from the ventricular system to another resorption site, bypassing the pathological obstruction by use of a CSF shunt. The most suitable diversion sites have been found to be the right atrium of the heart and the peritoneal cavity. Valves have been designed to hinder retrograde flow in the drainage system which could occur due to pressure differences between the intracranial cavity and the resorption site, e.g. in connection with increased chest and/or abdominal pressure in connection with e.g. cough or defecation.

Until the last 6 years the CSF shunts have been based on principle of maintaining a constant ICP regardless of the flow-rate of CSF. The CSF shunts have been constructed to off CSF-flow when the differential pressure between the in and the outlet of the CSF shunt was reduced to a predestined level, called the opening pressure of the shunt. This has been necessary in order to maintain a basal ICP due to the use of an unphysiological resorption sites located outside the intracranial cavity. Example of a such ICP shunt is shown in U.S. Pat. No. 4,904,236 which is a fluid flow control device for controlling the flow of fluid from one region of the body be drained to another region.

Clinical experience has proven that this principle of shunting is not an ideal solution. Sudden rises of the ICP, i. e. due to change of position, physical exercise, or pathological pressure waves result in excessive CSF drainage. This so-called hyperdrainage leads to subnormal ICP for shorter or longer periods of time. Several reports in the literature (Aschoff et al., 1995) point at problems due to this hyperdrainage, and especially the pronounced narrowing of the ventricles has been pointed out to be the main factor leading to malfunctioning of the implanted shunting device. The reason is that the ventricular walls may collapse around ventricular CSF shunt device, and particles (cells, debris may intrude into the shunt device.

This has led to the introduction of multiple designs of drains to be used in the ventricular cavity. An effect of these different drain designs on the complication rates of shun has not been proven.

In recent years, CSF shunt devices have been introduced which aim at regulating the flow rate of CSF, see e.g. U.S. Pat. No. 4,781,673 which describes a brain ventricle shunt system with flow rate switching means.

An alternative flow regulating mechanism of the Orbis Sigma shunt results in partial closure of the shunt at increases of the differential pressure above 10 mm Hg, and in reopening of the shunt when the differential pressure exceeds 35 mm Hg. It has been shown that this type of shunt indeed leads to a reduction of the complication rate of the system. Another shunt system, The Pudenz Delta valve, also hinders excessive CSF outflow at higher-pressure levels. U.S. Pat. No. 4,605,395 is an example of a shunt device comprising a non-linear hydraulic filter valve which closes in the event of large changes in flow rate.

Still, the above CSF shunt systems drain the CSF to a resorption site that is far from normal and to a site where the pressure difference over the shunt may differ substantially from the normal, physiological pressure ranges.

Occasional reports in the literature have described the use of ventriculo-superior sagittal shunts for the treatment of hydrocephalus (Hash et al., 1979 and Wen, 1981). In the article by Hash et al. it is concluded that the described technique wherein a low-low or extra-low pressure one way valve is used may be suitable for patients with high pressure hydrocephalus and of particular value in very ill or debilitated patients because of the rapidity with which it can be performed under local analgesia whereas its use in normal low pressure hydrocephalus must still be evaluated. This article is followed by a comment by the editor that there are a multitude of remaining critical questions. One of the problems not addressed in this study is overdrainage due to the fact that the used valve is not flow-restricting.

Wen et al., 1981, reports the treatment of fifty-two children with hydrocephalus with ventriculo-superior sagittal sinus shunts by use of a modified Pudenz tube. In this tube there is provided slits which provide an opening pressure of about 6 mm Hg. No clear conclusion can be drawn from this report except that shunting to the sagittal sinus does not inherit serious complications.

U.S. Pat. No. 5,000,731 describes a drain consisting essentially of a thin film and a ventricular tube having an open end and a closed bottom end for shunting cerebrospinal fluid to the subdural space on the surface of the brain. It is intended that through arachnoid lacerations or openings during the shunting procedure, the CSF in the subdural space will then enter into the subarachnoid space and be further absorbed by the arachnoid villi. Although this device has the benefit of being an intracranially located shunting device, it is draining the cerebrospinal fluid to an unphysiological place as it should be noted that under normal physiological conditions the subdural space is a potential space only which has gained its name due to the pathological occurrences of e.g. subdural haematoma which can occur in connection with lesions of the vascular system. Moreover, this system is only applicable in patients with normal resorption at the sagittal sinus, i.e. non-communicating hydrocephalus.

EP 066 685 describes a drain comprising a bundle of one or more microtubules, each being about 0.44 mm in diameter for controlling hydrocephalus comprising a plurality of pliable microtubular members for conducting cerebrospinal fluid from the cerebral ventricle to selected areas of the human body, e.g. to the subarachnoid space. Essentially, this patent relates to a draining system aiming at avoiding obstruction due to clotting of the draining system and is not flow-regulating.

WO 98/11934 describes a cerebrospinal fluid shunt system which drains surplus CSF to the sagittal sinus by means of a shunt with in-built resistance equal to normal values for CSF outflow-resistance and a unidirectional valve. It has surprisingly been found that this type of shunt drains insufficiently in patients with so-called normal pressure hydrocephalus. While functioning correctly, as measured by testing the inserted shunt, the shunt has failed to relieve the clinical symptoms in some of the shunted patients suffering from normal pressure hydrocephalus.

In normal pressure hydrocephalus a balance between the intracranial pressure and the stress on the ventricular walls has reached an equilibrium. The dilatation of the ventricles is followed by a decrease in the pressure necessary to maintain the dilatation, cf. the law of LaPlace (S.E. Børgesen et al., 1987).

Pressure waves (B-waves) still occur, but the amplitude is low. The resistance to outflow in this condition is still above the normal level of around 10 mm Hg/ml/min. In this condition, a drainage with a ventriculo-sagittal shunt with a resistance of 8–10 mmHg/ml/min will not lead to a decrease in the size of the ventricles. The low pressure necessary to maintain the stress on the ventricular walls means that the differential pressure from the ventricles to the sagittal sinus is very low, resulting in insufficient drainage of the surplus CSF. B-waves, which occur in the condition of normal pressure hydrocephalus will result in short time increases of the intracranial pressure, but a resistance to outflow above 8 mm Hg/ml/min means that only a fraction of the needed CSF drainage takes place. In this condition, shunts with a resistance to outflow in the range of 4–8 mm Hg/ml/min will be needed.

The same will be the case in children with very large ventricles, where the intracranial pressure may be too low to allow for a sufficiently pressure difference to establish sufficient CSF drainage.

SUMMARY OF THE INVENTION

Under normal conditions, the CSF is produced in the chorioid plexus in the ventricles. It flows through the ventricles, aqueduct and basal cisterns over the cerebral surface to the arachnoid villi, from where the CSF is absorbed into the sagittal sinus (including sinus transversus).

From measurements in 333 patients (Børgesen and Gjerris 1987) and 52 normal humans (Albeck, Børgesen et al.) it has been possible to establish the relationship between CSF production rate (FR), intracranial pressure (ICP), pressure in the sagittal sinus (Pss) and the resistance to outflow of CSF (Rout):

$$ICP = FR * Rout + PSS$$

The relation between the intracranial pressure and the formation rate is linear, and the production rate measured was found to be 0.3 ml/min. (Børgesen and Gjerris 1989). The detailed knowledge on CSF-dynamics, obtained in the laboratories at the Department of Neurosurgery, Rigshospitalet, Copenhagen, Denmark, has provided the necessary data which could make it possible to define a CSF shunt system that imitates the normal, physiological drainage of CSF. Moreover, it has been possible to relate the size of the ventricles with the intracranial pressure. It has been confirmed that the intracranial pressure decreases as the size of the ventricles increase. This means that in patients with very large ventricles, only a slight increase in intracranial pressure is needed to maintain the dilatation. In order to drain the ventricles for surplus CSF-accumulation, a shunt is needed with a very low resistance to outflow. However, until the present invention, it has not been proposed or contemplated to use this knowledge to design a cerebrospinal fluid shunt system as outlined in the following.

The present invention relates to a device for the treatment of hydrocephalus with very large ventricles and low intracranial pressure which device leads the CSF from the ventricles to the sagittal sinus beneath the sagittal suture. The present invention thus provides a low resistance CSF shunt system that treats the condition of normal pressure hydrocephalus by bypassing the pathological obstruction, but diverts the CSF into its normal resorption site, and the pressure difference over the CSF shunt system is similar to the physiological pressure differences between the ventricles and the resorption site, thus regulating the CSF flow to be within the normal range and avoiding complications due to hyperdrainage. Where appropriate, the present invention also relates to a method of treating normal pressure hydrocephalus by use of the cerebrospinal fluid shunt system of the invention.

Thus, the present invention provides a cerebrospinal fluid shunt system comprising a brain ventricle catheter device to insert into the brain ventricle so as to drain cerebrospinal fluid from the brain ventricle; a sinus catheter device to insert into the sinus sagittalis (including sinus transversus) for feeding the cerebrospinal fluid into the sinus system; a shunt main body member connected at one location thereof to said brain ventricle catheter device and at another location thereof to said sinus catheter device to provide fluidic communication between said brain ventricle catheter device and said sinus catheter device; and flow restricting passage means defined within the shunt body member to maintain a resistance to fluid flow of the shunt system of less than 8 mm Hg/ml/min, for example between 2 and 7.99 mm Hg/ml/min.

According to another aspect the present invention provides a cerebrospinal fluid shunt system comprising: a brain ventricle catheter sized to insert into a brain ventricle of a person so as to drain cerebrospinal fluid from the brain ventricle; a sinus catheter sized to insert into a sinus sagittalis (including the sinus transversus) of a person to feed cerebrospinal fluid into the sinus system; a main body connected at one location thereon to said brain ventricle catheter and at another location thereon to said sinus catheter to provide fluidic communication between said brain ventricle catheter and said sinus catheter; and a flow restricting passage defined within said main body to maintain a constant resistance to flow of the shunt system of less than 8 mm Hg/ml/min independent of an orientation of said main body.

Preferably, the resistance to flow of the shunt system is 2–7 mm Hg/ml/min, such as 4–6 mm Hg/ml/min, and presently most preferred about 5 mm Hg/ml/min.

The shunt system may comprise a check valve disposed within the shunt main body member to prevent the cerebrospinal fluid from flowing back from said sinus catheter device to said brain ventricle catheter device.

The flow restricting passage means may take many different forms, such as a plurality of tubes, a porous or fibrous mass, or a passage being restricted by co-extending fibres or rods arranged therein. In the presently preferred embodiment, however, the passage means is defined by a tubular passage having an internal radius exceeding 0.20 mm.

As a very important feature of the shunt system according to the present invention said flow restricting passage means may maintain the resistance to flow independent of an orientation of said shunt main body means. This means that the resistance is independent of whether the person using the shunt system is standing or laying.

In the presently preferred embodiment the brain ventricle catheter is connected to a first end of said main body, and said sinus catheter is connected to a second end of said main body.

The present invention further provides a cerebrospinal fluid shunt system comprising: means for insertion into the brain ventricle so as to drain cerebrospinal fluid from the brain ventricle; means for insertion into the sinus sagittalis or sinus system for feeding the cerebrospinal fluid into the sinus sagittalis; means for providing fluidic communication between said means for insertion into the brain ventricle and said means for insertion into the sinus sagittalis or sinus system, said means for providing fluidic communication connected at one location thereof to said means for insertion into the brain ventricle and at another location thereof to said means for insertion into the sinus sagittalis; and means, defined within said means for providing fluidic communication, for maintaining a resistance to flow of the shunt system of less than 8 mm Hg/ml/min.

According to a further aspect the present invention provides a cerebrospinal fluid shunt system comprising: a shunt body sized to extend between a brain ventricle of a person and a sinus sagittalis or sinus system of the person to provide fluid communication between the brain ventricle and the sinus sagittalis, said shunt body having a flow restricting structure defined within said shunt body to maintain a constant resistance to flow of the shunt body of less than 8 mm Hg/ml/min independent of an orientation of the shunt body.

The present invention also provides a method of implanting a cerebrospinal fluid shunt system said method comprising: providing a shunt member that includes at least one flow passage within the shunt member, the at least one flow passage defining a resistance to flow of the shunt system of less than 8 mm Hg/ml/min, for example between 2 and 7.99 mm Hg/ml/min; placing the shunt member subcutaneously on top of the calvarium of a patient, behind the coronal suture on one of side of the sagittal suture; connecting a first end of a first catheter to a first location on the shunt member; inserting a second end of the first catheter in the right ventricle via a first borehole; connecting a first end of a second catheter to a second location on the shunt member; and inserting a second end of the second catheter in the sinus sagittalis system via a second borehole, the shunt member providing fluidic communication between the first and second catheters. As mentioned above, the resistance to flow of the shunt system is preferably 2–7 mm Hg/ml/min, such as 4–6 mm Hg/ml/min, and most preferred about 5 mm Hg/ml/min.

According to a still further aspect the present invention provides a method of shunting cerebrospinal fluid from a brain ventricle to a sinus sagittalis system, comprising the steps of: providing a shunt member that includes at least one flow restricting passage within the shunt member, the at least one flow restricting passage defining a resistance to flow of the shunt system of less than 8 mm Hg/ml/min, such as between 2 and 7.99 mm Hg/ml/min; connecting a first catheter to a first location on the shunt member; connecting a second catheter to a second location on the shunt member, the shunt member providing fluidic communication between the first and second catheters; inserting the first catheter into the brain ventricle to drain cerebrospinal fluid from the brain ventricle; and inserting the second catheter into the sinus sagittalis system to feed the cerebrospinal fluid via the shunt member into the sinus sagittalis system.

In a preferred embodiment of the cerebrospinal fluid shunt system, the resistance is provided by one tubular flow passage restricting restricting means, the internal radius of which is less than about 0.20 mm and the flow-restricting part of the tubular flow passage restricting means has a length, which is calculated according to the law of Hagen-Poiseulle taking into consideration the aim to provide a resistance to CSF-outflow through the shunt of less than 8 mm Hg/ml/min, such as about 5 mm Hg/ml/min. In particularly preferred embodiments, the internal radius of the tubular flow passage restricting means is e.g. about 0.10 mm, about 0.11 mm, about 0.12 mm, about 0.13 mm, about 0.14 mm, about 0.15 mm, about 0.16 mm, about 0.17 mm, about 0.18 mm or about 0.19 mm and the length is calculated accordingly.

The length can be calculated as follows:

$$L=((ICP-Pss)*\pi*R4)/8*F*V \text{ Hagen-Poiseulle's law,}$$

wherein ICP is the intracranial pressure, Pss is the pressure in the sagittal sinus, F is the flow rate of the cerebrospinal fluid and V is the viscosity of the cerebro-spinal fluid.

The resistance may be provided by more than one tubular flow passage restricting means, e.g. the tubular flow passage restricting means may be divided in sections so that the resistance is provided by several, e.g. two or three or a larger number of tubular flow passage restricting means connected in series, or the resistance may be provided by several, e.g. two or three tubular or a larger number of flow passage restricting means connected in parallel. Preferably, the tubular flow passage restricting means consists of only one tubular flow passage restricting means. In any event, the person of ordinary skill in the art is capable of calculating the resistance to flow using essentially Hagen-Poiseulle's law as a guidance. The results of the practical investigations have shown that the relationship between the resistance to outflow of CSF (Rout) and the length of the tubular flow passage restricting means is not completely linear, but for practical purposes Hagen-Poiseulle's law can be used to calculate appropriate dimensions of the tubular flow passage restricting means also when two or three or a larger number of tubular flow passage restricting means are connected in series or in parallel.

In general, the tubular flow passage restricting means will have a length within the range of 3.5 mm to 83.8 mm, preferably within the range of 17.7 mm to 26.5 mm, such as about 22.1 mm, either in itself or defined within said shunt main body. This length may be divided in two or more individual segments, if considered appropriate, as discussed above.

Optionally, the cerebrospinal fluid shunt system further comprises one or more check valve means disposed within said shunt main body for preventing said cerebrospinal fluid from flowing back from said sinus catheter to said brain ventricle catheter.

By designing the shunt to exert a substantially constant resistance to outflow at the normal level, and by using the sagittal sinus as the resorption site, the drainage of CSF is regulated by the normal pressure differences between the production and the resorption sites. Excessive increases of the intracranial pressure are paralleled by increases also in the sagittal sinus, and the CSF outflow through the shunt is impeded by a resistance in the low to normal range. Hyperdrainage is then totally avoided.

The innovation is thus to use the recently defined levels of the normal resistance to CSF outflow and create a resistance to CSF-outflow in the shunt sufficiently low to allow for CSF outflow in spite of the low or normal intracranial pressure. By using the sagittal sinus as the recipient site, physiological increases of the intracranial pressure will not increase the differential pressure over the shunt. Posture related changes in the differential pressure as seen in shunts leading the CSF to the right atrium of the heart or to the peritoneal cavity are completely avoided. Overdrainage, which is the most frequent reason for shunt failure in conventional shunts, is thus also avoided.

Inclusion of check valve means in the shunt will hinder any reflux of blood from the sagittal sinus into the shunt (or the ventricles). The check valve means are constructed in such a way that there is substantially no resistance to the CSF flow through the shunt and has substantially no pressure threshold to be overcome for the intracranial pressure. The check valve means may be a ball valve which can be with guided rigid valve members, e.g. shaped as rings, or be with flexible valve members e.g. with tongue-shaped laminae. Preferably, the check valve means is a mitral silicone valve.

In a presently preferred embodiment, the shunt comprises of a catheter for the ventricle, a body containing the resistance device and check valve means substantially without any inherited resistance compared to the resistance in the flow passage resistance or restricting device, and a drain to be introduced into the sagittal sinus.

BRIEF DESCRIPTION OF THE DRAWINGS

The invention will now be further described with reference to the drawings,
wherein.

DETAILED DESCRIPTION OF THE PREFERRED EMBODIMENTS

Figure 1:
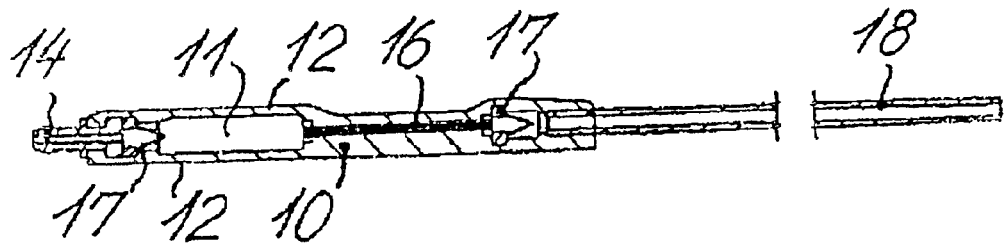
FIG. 1 is a longitudinal sectional view of an embodiment of the shunt system according to the invention.
Figure 2:
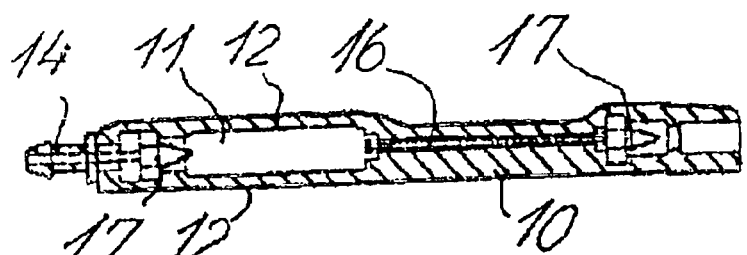
FIG. 2 is a sectional view of the shunt body shown in FIG. 1.
Figure 3:
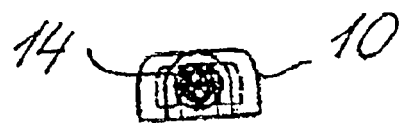
FIG. 3 is an end view of the shunt body shown in FIG. 2.
Figure 4:
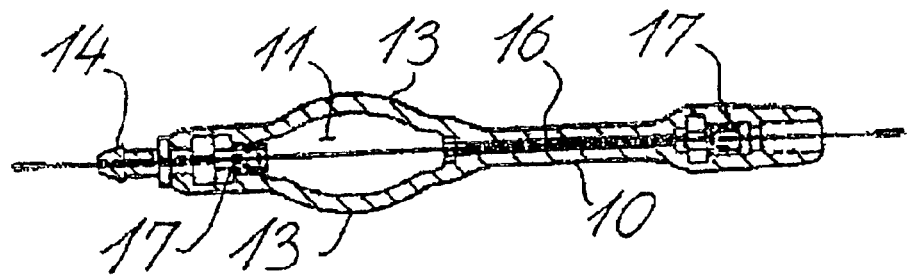
FIG. 4 is a longitudinal sectional view of the shunt body taken at right angles to the section shown in FIG. 2.
Figure 5:
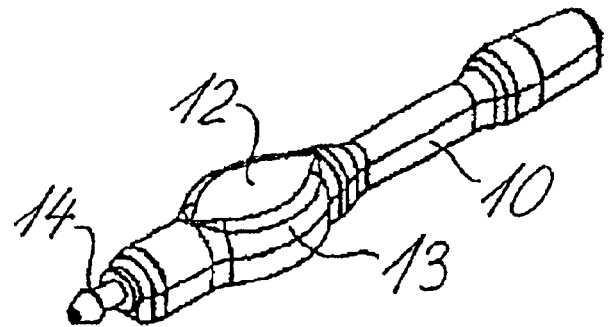
FIG. 5 is a perspective view of the shunt body shown in FIGS. 2–4.

FIGS. 1–5 illustrate an embodiment of the cerebrospinal fluid shunt system according to the invention. The shunt system comprises a shunt body 10, which is made from a suitable material, such as a silicone rubber. An antechamber 11 may have opposite flat walls 12 made from hard silicone rubber, and opposite domed walls 13, which are made from soft, perforatable, self-healing silicone rubber. At the proximal end (the top end) the chamber walls end in a tip 14, to which a ventricular drain or catheter 15 can be connected and secured. At the distal end of the chamber 11 an inlet to a tubular flow restriction 16 is formed. A check valve or non-return valve 17 are arranged at the entrance to the antechamber 11 as well as at the outlet of the tubular flow restriction 16. Fluidic connection to the sinus sagittalis is provided by a tubular drain 18.

The ventricular drain 15 is attached to the tip or inlet connector 14, which is provided with an annular bead. The length of the connector 14 is generally about 5 mm. The drain 15 is secured the usual way e.g. by means of a ligature. The antechamber 11 is in connection with the tubular flow restriction 16.

The tubular flow restriction 16 is dimensioned according to Hagen-Poiseulle's law to a resistance to flow of less than 8 mm Hg/ml/min. The tubular flow passage restriction is preferably substantially straight or linear, and the inner walls of the restriction are preferably substantially smooth. The material from which the walls of the tubular flow restriction is made may, for example, be hard silicone rubber or HD polyethylene (e.g. gas sterilized polypropylene), polycarbonate, polysulfone, polystyrene or PVC. Alternatively, the tubular restriction can be from titanium.

The drain 18 for the sagittal sinus may, for example, be titanium tube or silicone rubber tube. The distal 5 mm of the tube will generally have an outer diameter of 2 mm and an inner diameter of 1.5 mm. The part of the drain that goes through the skull has generally an outer diameter of 3 mm, the inner diameter is 1.5 mm. The part of the drain with the largest diameter may be shortened to fit the distance from the body of the shunt to the hole over the sagittal sinus.

Alternatively, the drain 18 may comprise a titanium tube with an inner diameter of 1.5 mm and a length of 20 mm attached to a silicone rubber tube with outer/inner diameter of 3/1.5 mm and a length of 60 mm. The titanium tube is readily inserted via a 2 mm wide borehole through the bone covering the sagittal sinus. A stilet in the tube allows the inserted tube to be angled somewhat to lead the silicone rubber tube following the surface of the skull to the body of the shunt.

Figure 6:
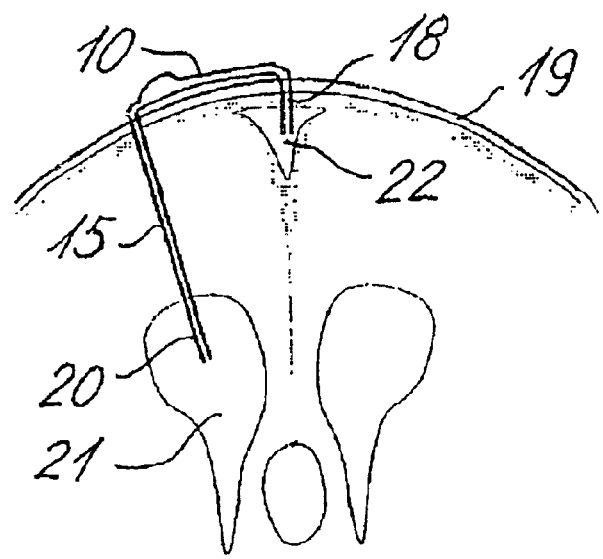
FIG. 6 is a partial cross-sectional view of the head of a person, in which the shunt system illustrated in FIGS. 1–5 has been installed.
Figure 7:
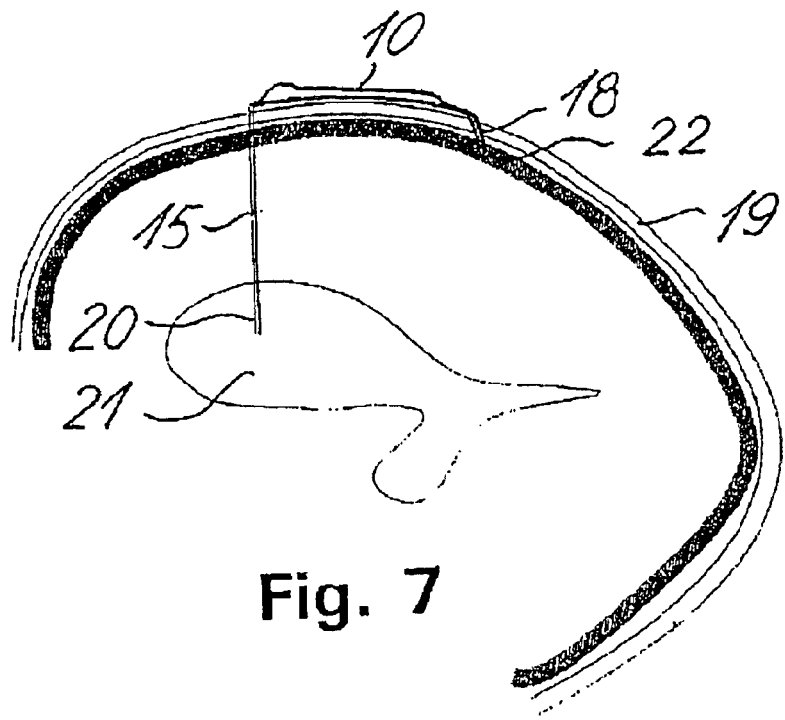
FIG. 7 is a longitudinal sectional view of the head of a person, in which the shunt system illustrated in FIGS. 1–5 has been installed.

FIGS. 6 and 7 show the principles of the location of the shunt device or system. The shunt body 10 is placed subcutaneously on the top of the calvarium, behind the coronal suture on the right (or left) side of the sagittal suture, see FIG. 6. Via a bored hole through the skull 19 a catheter 20 is inserted in the right (or left) ventricle 21 and via the ventricular drain or silicone rubber tube 15 it is connected to the shunt body 10. A small hole (2–3 mm in diameter) is bored through the skull 19 directly over the sagittal sinus 22, running in the midline beneath the readily identifiable sagittal suture. The drain 18 of substantially the same outer diameter as the inner diameter of the borehole is introduced into the sagittal sinus 22 and is connected to the "distal" end of the shunt body 10. Suitable ventricular drains are well-known within the art, and the drain 15 can e.g. be a plain silicone rubber drain with an outer diameter of about 3 mm. Standard produced drains may be preferred.

Figure 8:
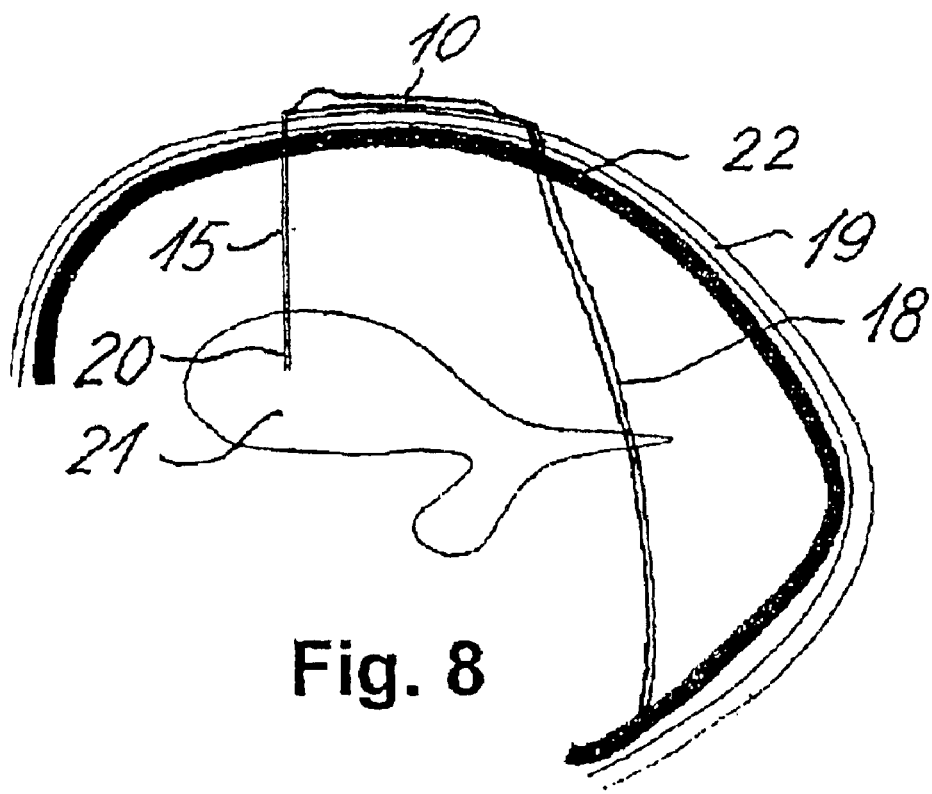
FIG. 8 is a sectional view as that shown in FIG. 7, where the sinus catheter has been inserted in the transverse sinus.

In FIG. 8 the sinus catheter is inserted in the transverse sinus. The shunt body 10 is placed subcutaneously between a frontal borehole for receiving the drain 15 and the transverse sinus. The widest part of the transverse sinus is behind the ear of the patient, where an osseous prominence indicate the location. A borehole is made directly over the sinus, preferably by using a trephine or a high-speed air drill.

What is claimed is:

1. A cerebrospinal fluid shunt system comprising
   a brain ventricle catheter device to insert into the brain ventricle so as to drain cerebrospinal fluid from the brain ventricle;
   a sinus catheter device to insert into the sinus sagittalis system for feeding the cerebrospinal fluid into the sinus sagittalis system;
   a shunt body member connected at one location thereof to said brain ventricle device
   and at another location thereof to said sinus catheter device to provide fluidic communication between said brain ventricle catheter device and said sinus catheter device; and
   means for restricting fluid flow through said shunt system of less than 8 mm Hg/ml/min, said means comprising a flow restricting passage within said shunt body member between the brain catheter device and the sinus catheter device.

2. A cerebrospinal fluid shunt system according to claim 1, wherein the resistance to flow of the shunt system is 2–7 mm Hg/ml/min.

3. A cerebrospinal fluid shunt system according to claim 2, wherein the resistance to flow of the shunt system is maintained constant at 4–6 mm Hg/ml/min, and wherein said flow restricting passage means is substantially straight or linear, and is rigid with a smooth inner wall.

4. A cerebrospinal fluid shunt system according to claim 3, wherein the resistance to flow of the shunt system is maintained constant at about 5 mm Hg/ml/min, and wherein said flow restricting passage means is substantially straight or linear, and is rigid with a smooth inner wall.

5. A cerebrospinal fluid shunt system according to claim 1 further comprising a check valve disposed within the shunt body member to prevent the cerebrospinal fluid from flowing back from said sinus catheter device to said brain ventricle catheter device.

6. A cerebrospinal fluid shunt system according to claim 1, wherein the flow restricting passage means is defined by a tubular passage having an internal radius exceeding 0.20 mm.

7. A cerebrospinal fluid shunt system according to claim 1, wherein said flow restricting passage means maintains the resistance to flow independent of an orientation of said shunt body member.

8. A cerebrospinal fluid shunt system comprising:
   a brain ventricle catheter sized to insert into a brain ventricle of a person so as to drain cerebrospinal fluid from the brain ventricle;
   a sinus catheter sized to insert into a sinus sagittalis system of a person to feed cerebrospinal fluid into the sinus sagittalis system;
   a main body connected at one location thereon to said brain ventricle catheter and at another location thereon to said sinus catheter to provide fluidic communication between said brain ventricle catheter and said sinus catheter; and
   a flow restricting passage defined within said main body to maintain a constant resistance to flow of the shunt system of less than 8 mm Hg/ml/min independent of an orientation of said main body.

9. A cerebrospinal fluid shunt system according to claim 8, wherein the resistance to flow of the shunt system is 2–7 mm Hg/ml/min.

10. A cerebrospinal fluid shunt system according to claim 9, wherein the resistance to flow of the shunt system is 4–6 mm. Hg/ml/min.

11. A cerebrospinal fluid shunt system according to claim 10, wherein the resistance to flow of the shunt system is about 5 mm Hg/ml/min.

12. A cerebrospinal fluid shunt system according to claim 8 further comprising a check valve disposed within said shunt main body to prevent the cerebrospinal fluid from flowing back from said sinus catheter system to said brain ventricle catheter.

13. A cerebrospinal fluid shunt system according to claim 8, wherein the flow restricting passage is defined by a tubular passage having an internal radius exceeding 0.20 mm.

14. A cerebrospinal fluid shunt system according to claim 8, wherein said brain ventricle catheter is connected to a first end of said main body, and said sinus catheter is connected to a second end of said main body.

15. A cerebrospinal fluid shunt system comprising:
   means for insertion into the brain ventricle so as to drain cerebrospinal fluid from the brain ventricle;
   means for insertion into the sinus sagittalis system for feeding the cerebrospinal fluid into the sinus sagittalis system;
   means for providing fluidic communication between said means for insertion into the brain ventricle and said means for insertion into the sinus sagittalis system, said
   means for providing fluidic communication connected at one location thereof to said means for insertion into the brain ventricle and at another location thereof to said means for insertion into the sinus sagittalis system; and
   means, defined within said means for providing fluidic communication, for maintaining a resistance to flow of the shunt system of less than 8 mm Hg/ml/min.

16. A cerebrospinal fluid shunt system according to claim 15, wherein the resistance to flow of the shunt system is 2–7 mm Hg/ml/min.

17. A cerebrospinal fluid shunt system according to claim 16, wherein the resistance to flow of the shunt system is 4–6 mm Hg/ml/min.

18. A cerebrospinal fluid shunt system according to claim 17, wherein the resistance to flow of the shunt system is about 5 mm Hg/ml/min.

19. A cerebrospinal fluid shunt system according to claim 15 having means, disposed within said means for providing fluidic communication, for preventing the cerebrospinal fluid from flowing back from said means for insertion into the sinus sagittalis system to said means for insertion into the brain ventricle.

20. A cerebrospinal fluid shunt system according to claim 15, wherein said means for maintaining a resistance to flow is defined by a tubular passage having an internal radius exceeding 0.20 mm.

21. A cerebrospinal fluid shunt system according to claim 15, wherein said means for maintaining a resistance to flow maintains a resistance to flow of the shunt system of less than 8 mm Hg/ml/min, independent of an orientation of said means for providing fluidic communication.

22. A cerebrospinal fluid shunt system comprising:
   a shunt body sized to extend between a brain ventricle of a person and a sinus sagittalis system of the person to provide fluid communication between the brain ventricle and the sinus sagittalis system, said shunt body having a flow restricting structure defined within said shunt body to maintain a constant resistance to flow of the shunt body of less than 8 mm Hg/ml/min independent of an orientation of the shunt body.

23. A cerebrospinal fluid shunt system according to claim 22, wherein the resistance to flow of the shunt system is 2–7 mm Hg/ml/min.

24. A cerebrospinal fluid shunt system according to claim 22, wherein the resistance to flow of the shunt system is 4–6 mm Hg/ml/min.

25. A cerebrospinal fluid shunt system according to claim 24, wherein the resistance to flow of the shunt system is about 5 mm Hg/ml/min.

26. A method of implanting a cerebrospinal fluid shunt system comprising:
    providing a shunt member that includes at least one flow restricting passage within the shunt member, the at least one flow passage defining a resistance to flow of the shunt system of less than 8 mm Hg/ml/min;
    placing the shunt member subcutaneously on top of the calvarium of a patient, behind the coronal suture on one of side of the sagittal suture;
    connecting a first end of a first catheter to a first location on the shunt member;
    inserting a second end of the first catheter in the right ventricle via a first borehole;
    connecting a first end of a second catheter to a second location on the shunt member; and
    inserting a second end of the second catheter in the sinus sagittalis system via a second borehole, the shunt member providing fluidic communication between the first and second catheters.

27. A method according to claim 26, wherein the resistance to flow of the shunt system is 2–7 mm Hg/ml/min.

28. A method according to claim 27, wherein the resistance to flow of the shunt system is 4–6 mm Hg/ml/min.

29. A method according to claim 28, wherein the resistance to flow of the shunt system is about 5 mm Hg/ml/min.

30. A method of implanting a cerebrospinal fluid shunt system comprising:
    providing a shunt member that includes at least one flow restricting passage
    within the shunt member, the at least one flow restricting passage defining a resistance to flow of the shunt system of less than 8 mm Hg/ml/min;
    placing the shunt member subcutaneously on top of the calvarium of a patient, behind the coronal suture on one of side of the sagittal suture;
    connecting a first end of a first catheter to a first location on the shunt member; inserting a second end of the first catheter in the right ventricle via a first borehole; connecting a first end of a second catheter to a second location on the shunt member, and
    inserting a second end of the second catheter in a sinus transversus via a second borehole, the shunt member providing fluidic communication between the first and second catheters.

31. A method of shunting cerebrospinal fluid from a brain ventricle to a sinus sagittalis system, comprising the steps of:
    providing a shunt member that includes at least one flow restricting passage within the shunt member, the at least one flow restricting passage defining a resistance to flow of the shunt system of less than 8 mm Hg/ml/min;
    connecting a first catheter to a first location on the shunt member;
    connecting a second catheter to a second location on the shunt member, the shunt member providing fluidic communication between the first and second catheters;
    inserting the first catheter into the brain ventricle to drain cerebrospinal fluid from the brain ventricle; and
    inserting the second catheter into the sinus sagittalis system to feed the cerebrospinal fluid via the shunt member into the sinus sagittalis system.

32. A method of shunting cerebrospinal fluid according to claim 31, wherein the resistance to flow of the shunt system is 2–7 mm Hg/ml/min.

33. A method of shunting cerebrospinal fluid according to claim 32, wherein the resistance to flow of the shunt system is 4–6 mm Hg/ml/min.

34. A method of shunting cerebrospinal fluid according to claim 33, wherein the resistance to flow of the shunt system is about 5 mm Hg/ml/min.

35. A method of shunting cerebrospinal fluid according to claim 31, wherein the resistance to flow is maintained at less than 8 mm Hg/ml/min, independent of an orientation of the shunt member.

36. A method of shunting cerebrospinal fluid according to claim 31, further comprising the step of preventing cerebrospinal fluid from flowing back from the second catheter to the first catheter via a check valve disposed within the shunt member.

37. A method of shunting cerebrospinal fluid according to claim 31, wherein the at least one flow passage has an internal radius exceeding 0.20 mm.

38. A method of shunting cerebrospinal fluid from a brain ventricle to a sinus transversus, comprising the steps of:
    providing a shunt member that includes at least one flow restricting passage within the shunt member, the at least one flow restricting passage defining a resistance to flow of the shunt system of less than 8 mm Hg/ml/min;
    connecting a first catheter to a first location on the shunt member;
    connecting a second catheter to a second location on the shunt member, the shunt member providing fluidic communication between the first and second catheters;
    inserting the first catheter into the brain ventricle to drain cerebrospinal fluid from the brain ventricle; and
    inserting the second catheter into a sinus transversus to feed the
    cerebrospinal fluid via the shunt member into the sinus transversus.

39. A cerebrospinal fluid system according to claim 1, wherein the resistance to fluid flow of the shunt system is maintained at a fixed constant value that is less than 8 mm Hg/ml/min.

* * * * *